US012295791B2

(12) United States Patent
Yamamoto et al.

(10) Patent No.: US 12,295,791 B2
(45) Date of Patent: May 13, 2025

(54) ULTRASOUND DIAGNOSTIC APPARATUS, CONTROL METHOD FOR ULTRASOUND DIAGNOSTIC APPARATUS, AND PROCESSOR FOR ULTRASOUND DIAGNOSTIC APPARATUS

(71) Applicant: FUJIFILM Corporation, Tokyo (JP)

(72) Inventors: Katsuya Yamamoto, Kanagawa (JP); Tomoki Inoue, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 168 days.

(21) Appl. No.: 18/064,221

(22) Filed: Dec. 9, 2022

(65) Prior Publication Data
US 2023/0103571 A1    Apr. 6, 2023

Related U.S. Application Data

(63) Continuation of application No. PCT/JP2021/009483, filed on Mar. 10, 2021.

(30) Foreign Application Priority Data

Jul. 1, 2020  (JP) ................................. 2020-113921

(51) Int. Cl.
*A61B 8/00* (2006.01)

(52) U.S. Cl.
CPC ............ *A61B 8/467* (2013.01); *A61B 8/4245* (2013.01); *A61B 8/4427* (2013.01); *A61B 8/463* (2013.01); *A61B 8/465* (2013.01)

(58) Field of Classification Search
CPC ... A61B 8/4245; A61B 8/4427; A61B 8/4472; A61B 8/463; A61B 8/465; A61B 8/467; A61B 8/54; G01S 7/52073; G01S 7/52084

See application file for complete search history.

(56) References Cited

U.S. PATENT DOCUMENTS 5,544,654 A    8/1996  Murphy et al.
2002/0173721 A1    11/2002  Grunwald et al.
(Continued)

FOREIGN PATENT DOCUMENTS

CN    101959463 A    1/2011
CN    202235453 U    5/2012
(Continued)

OTHER PUBLICATIONS

An Office Action mailed by China National Intellectual Property Administration on Jul. 17, 2024, which corresponds to Chinese Patent Application No. 202180045765.5 and is related to U.S. Appl. No. 18/064,221; with English language translation.
(Continued)

*Primary Examiner* — Mark D Remaly
(74) *Attorney, Agent, or Firm* — Studebaker Brackett PLLC

(57) ABSTRACT

An ultrasound diagnostic apparatus (1) performs switching between a normal screen display mode and a full-screen display mode by performing a mode switching operation on a diagnostic apparatus main body (3) or an ultrasound probe (2), the normal screen display mode being a mode in which an ultrasound image generated by an image generation unit (22) and an operation panel for operating the ultrasound diagnostic apparatus (1) are displayed on a monitor (24) and an operation of the ultrasound diagnostic apparatus (1) is performed via the operation panel, and the full-screen display mode being a mode in which only the ultrasound image generated by the image generation unit (22) is displayed on the monitor (24) and an operation of the ultrasound diagnostic apparatus (1) by using a voice is possible.

17 Claims, 7 Drawing Sheets

(56) References Cited

U.S. PATENT DOCUMENTS

| | | | |
|---|---|---|---|
| 2008/0253589 A1* | 10/2008 | Trahms | G01S 7/52084 |
| | | | 704/E15.045 |
| 2009/0043195 A1* | 2/2009 | Poland | A61B 8/465 |
| | | | 600/437 |
| 2011/0043434 A1 | 2/2011 | Roncalez et al. | |
| 2013/0158408 A1 | 6/2013 | Tsuda et al. | |
| 2013/0225999 A1 | 8/2013 | Banjanin et al. | |
| 2014/0024939 A1 | 1/2014 | Kato et al. | |
| 2015/0327841 A1* | 11/2015 | Banjanin | A61B 8/4263 |
| | | | 600/443 |
| 2018/0168548 A1 | 6/2018 | Chiang et al. | |
| 2018/0368812 A1 | 12/2018 | Kim et al. | |
| 2021/0030399 A1 | 2/2021 | Tsubota et al. | |
| 2021/0055396 A1 | 2/2021 | Karasawa | |

FOREIGN PATENT DOCUMENTS

| | | |
|---|---|---|
| CN | 103228220 A | 7/2013 |
| CN | 104023645 A | 9/2014 |
| CN | 110064191 A | 7/2019 |
| JP | H11-197142 A | 7/1999 |
| JP | 2001-276062 A | 10/2001 |
| JP | 2011-104109 A | 6/2011 |
| JP | 2013-111203 A | 6/2013 |
| JP | 2020-92830 A | 6/2020 |
| WO | 2019/220979 A1 | 11/2019 |
| WO | 2019/225417 A1 | 11/2019 |

OTHER PUBLICATIONS

The extended European search report issued by the European Patent Office on Nov. 3, 2023, which corresponds to European Patent Application No. 21833379.7-1126 and is related to U.S. Appl. No. 18/064,221.

International Search Report issued in PCT/JP2021/009483; mailed May 11, 2021.

International Preliminary Report on Patentability and Written Opinion issued in PCT/JP2021/009483; issued Dec. 15, 2022.

An Office Action; "Notice of Reasons for Refusal," mailed by the Japanese Patent Office on Nov. 7, 2023, which corresponds to Japanese Patent Application No. 2022-533682 and is related to U.S. Appl. No. 18/064,221; with English language translation.

An Office Action; mailed by the China National Intellectual Property Administration of the People's Republic of China on Feb. 18, 2025, which corresponds to Chinese Patent Application No. 202180045765.5 and is related to U.S. Appl. No. 18/064,221.

* cited by examiner

ULTRASOUND DIAGNOSTIC APPARATUS, CONTROL METHOD FOR ULTRASOUND DIAGNOSTIC APPARATUS, AND PROCESSOR FOR ULTRASOUND DIAGNOSTIC APPARATUS

CROSS-REFERENCE TO RELATED APPLICATIONS

This application is a Continuation of PCT International Application No. PCT/JP2021/009483 filed on Mar. 10, 2021, which claims priority under 35 U.S.C. § 119(a) to Japanese Patent Application No. 2020-113921 filed on Jul. 1, 2020. The above applications are hereby expressly incorporated by reference, in its entirety, into the present application.

BACKGROUND OF THE INVENTION

1. Field of the Invention

The present invention relates to an ultrasound diagnostic apparatus, a control method for an ultrasound diagnostic apparatus, and a processor for an ultrasound diagnostic apparatus capable of performing voice recognition.

In the related art, an examination of the inside of a subject is performed using an ultrasound diagnostic apparatus. In such an examination, for example, as in a case where an ultrasound probe is fixed in one hand of a user and the inside of the subject is observed while the other hand of the user is used to insert a puncture needle into the subject, both hands of a user may not be available during an examination or a procedure using the ultrasound diagnostic apparatus. In order to operate the ultrasound diagnostic apparatus even in this state, for example, an ultrasound diagnostic apparatus that recognizes a voice of a user and controls an operation according to the recognized voice has been developed as disclosed in JP1999-197142A (JP H11-197142A).

SUMMARY OF THE INVENTION

On the other hand, for example, in a medical site at a remote place away from a hospital, such as a site for home nursing, a so-called handheld type ultrasound diagnostic apparatus including an ultrasound probe and a portable diagnostic apparatus main body connected to the ultrasound probe may be used. In such a handheld type ultrasound diagnostic apparatus, the diagnostic apparatus main body often includes a monitor with a touch sensor. The monitor of the handheld type ultrasound diagnostic apparatus has a small size in many cases, and it is necessary to display a user interface for allowing a user to perform an input operation on the monitor in addition to the captured ultrasound image. For this reason, as in the technique disclosed in JP1999-197142A (JP H11-197142A), even in a case where the user can perform an input operation by voice recognition, it may be difficult for the user to confirm the ultrasound image displayed on the monitor, and it may be difficult to smoothly perform ultrasound diagnosis.

The present invention has been made to solve such problems in the related art, and an object of the present invention is to provide an ultrasound diagnostic apparatus, a control method for an ultrasound diagnostic apparatus, and a processor for an ultrasound diagnostic apparatus capable of allowing a user to smoothly perform ultrasound diagnosis.

In order to achieve the above object, according to an aspect of the present invention, there is provided a handheld type ultrasound diagnostic apparatus including: an ultrasound probe; and a diagnostic apparatus main body connected to the ultrasound probe, in which the diagnostic apparatus main body includes an image generation unit that generates an ultrasound image based on a reception signal acquired by using the ultrasound probe, a monitor with a touch sensor that displays the ultrasound image, a microphone for inputting a voice, and a voice recognition unit that recognizes a voice which is input via the microphone, and the diagnostic apparatus main body performs switching between a normal screen display mode and a full-screen display mode by performing a mode switching operation on the diagnostic apparatus main body or the ultrasound probe, the normal screen display mode being a mode in which the ultrasound image generated by the image generation unit and an operation panel for operating the ultrasound diagnostic apparatus are displayed on the monitor and an operation of the ultrasound diagnostic apparatus is performed via the operation panel, and the full-screen display mode being a mode in which only the ultrasound image generated by the image generation unit is displayed on the monitor and an operation of the ultrasound diagnostic apparatus by using a voice is possible.

Preferably, the mode switching operation for switching from the normal screen display mode to the full-screen display mode is a touch operation on a screen of the monitor or an input operation of a predetermined first voice.

Alternatively, the ultrasound diagnostic apparatus further includes a shake detection unit that detects a shake operation on the diagnostic apparatus main body or the ultrasound probe. In this case, the mode switching operation for switching from the normal screen display mode to the full-screen display mode may be the shake operation.

In this case, the ultrasound diagnostic apparatus further includes a vibration sensor that detects a vibration of the diagnostic apparatus main body or the ultrasound probe, and the shake detection unit can detect the shake operation based on the vibration of the diagnostic apparatus main body or the ultrasound probe that is detected by the vibration sensor.

Alternatively, the shake detection unit can detect the shake operation by analyzing ultrasound images including a plurality of continuous frames generated by the image generation unit.

Preferably, the mode switching operation for switching from the full-screen display mode to the normal screen display mode is a touch operation on a screen of the monitor or an input operation of a predetermined second voice different from the first voice.

Alternatively, the ultrasound diagnostic apparatus further includes a shake detection unit that detects a shake operation on the diagnostic apparatus main body or the ultrasound probe, and the mode switching operation for switching from the full-screen display mode to the normal screen display mode may be the shake operation.

In this case, the ultrasound diagnostic apparatus further includes a vibration sensor that detects a vibration of the diagnostic apparatus main body or the ultrasound probe, and the shake detection unit can detect the shake operation based on the vibration of the diagnostic apparatus main body or the ultrasound probe that is detected by the vibration sensor.

Alternatively, the shake detection unit can detect the shake operation by analyzing ultrasound images including a plurality of continuous frames generated by the image generation unit.

Further, in a case where the mode switching operation for switching from the normal screen display mode to the full-screen display mode is the shake operation, the mode switching operation for switching from the full-screen display mode to the normal screen display mode can also be the shake operation.

In a case where the mode switching operation for switching from the full-screen display mode to the normal screen display mode is the input operation of the second voice, a touch operation on a screen of the monitor may be enabled in the normal screen display mode, and a touch operation on a screen of the monitor may be disabled in the full-screen display mode.

Further, even in a case where the mode switching operation for switching from the full-screen display mode to the normal screen display mode is the shake operation, a touch operation on a screen of the monitor may be enabled in the normal screen display mode, and a touch operation on a screen of the monitor may be disabled in the full-screen display mode.

The ultrasound diagnostic apparatus further includes a probe type recognition unit that recognizes a type of the ultrasound probe. In the full-screen display mode, a display according to the type of the ultrasound probe that is recognized by the probe type recognition unit can be performed on the monitor.

Further, the ultrasound diagnostic apparatus further includes an ultrasound transmission/reception control unit that controls transmission of an ultrasound beam and reception of an ultrasound echo by the ultrasound probe. In the full-screen display mode, the ultrasound transmission/reception control unit can change a position of a transmission focus of the ultrasound beam according to a display depth of the ultrasound image on the monitor.

According to another aspect of the present invention, there is provided a control method for an ultrasound diagnostic apparatus including an ultrasound probe and a diagnostic apparatus main body connected to the ultrasound probe, the method including: generating an ultrasound image based on a reception signal acquired by using the ultrasound probe; and performing switching between a normal screen display mode and a full-screen display mode by performing a mode switching operation on the diagnostic apparatus main body or the ultrasound probe, the normal screen display mode being a mode in which the generated ultrasound image and an operation panel for operating the ultrasound diagnostic apparatus are displayed on a monitor of the diagnostic apparatus main body and an operation of the ultrasound diagnostic apparatus is performed via the operation panel, and the full-screen display mode being a mode in which only the generated ultrasound image is displayed on the monitor and an operation of the ultrasound diagnostic apparatus by using a voice is possible.

According to still another aspect of the present invention, there is provided a processor for a handheld type ultrasound diagnostic apparatus that includes an ultrasound probe and a diagnostic apparatus main body connected to the ultrasound probe, the processor being configured to execute a process including: generating an ultrasound image based on a reception signal acquired by using the ultrasound probe; and performing switching between a normal screen display mode and a full-screen display mode by performing a mode switching operation on the diagnostic apparatus main body or the ultrasound probe, the normal screen display mode being a mode in which the generated ultrasound image and an operation panel for operating the ultrasound diagnostic apparatus are displayed on a monitor of the diagnostic apparatus main body and an operation of the ultrasound diagnostic apparatus is performed via the operation panel, and the full-screen display mode being a mode in which only the generated ultrasound image is displayed on the monitor and an operation of the ultrasound diagnostic apparatus by using a voice is possible.

According to the present invention, an ultrasound diagnostic apparatus includes a monitor with a touch sensor that displays an ultrasound image and a voice recognition unit that recognizes a voice which is input via a microphone, and performs switching between a normal screen display mode and a full-screen display mode by performing a mode switching operation on a diagnostic apparatus main body or an ultrasound probe, the normal screen display mode being a mode in which the ultrasound image generated by an image generation unit and an operation panel for operating the ultrasound diagnostic apparatus are displayed on the monitor and an operation of the ultrasound diagnostic apparatus is performed via the operation panel, and the full-screen display mode being a mode in which only the ultrasound image generated by the image generation unit is displayed on the monitor and an operation of the ultrasound diagnostic apparatus by using a voice is possible. Thereby, a user can smoothly perform ultrasound diagnosis.

DESCRIPTION OF THE PREFERRED EMBODIMENTS

Hereinafter, embodiments of the present invention will be described with reference to the accompanying drawings.

Embodiment 1

Figure 1:
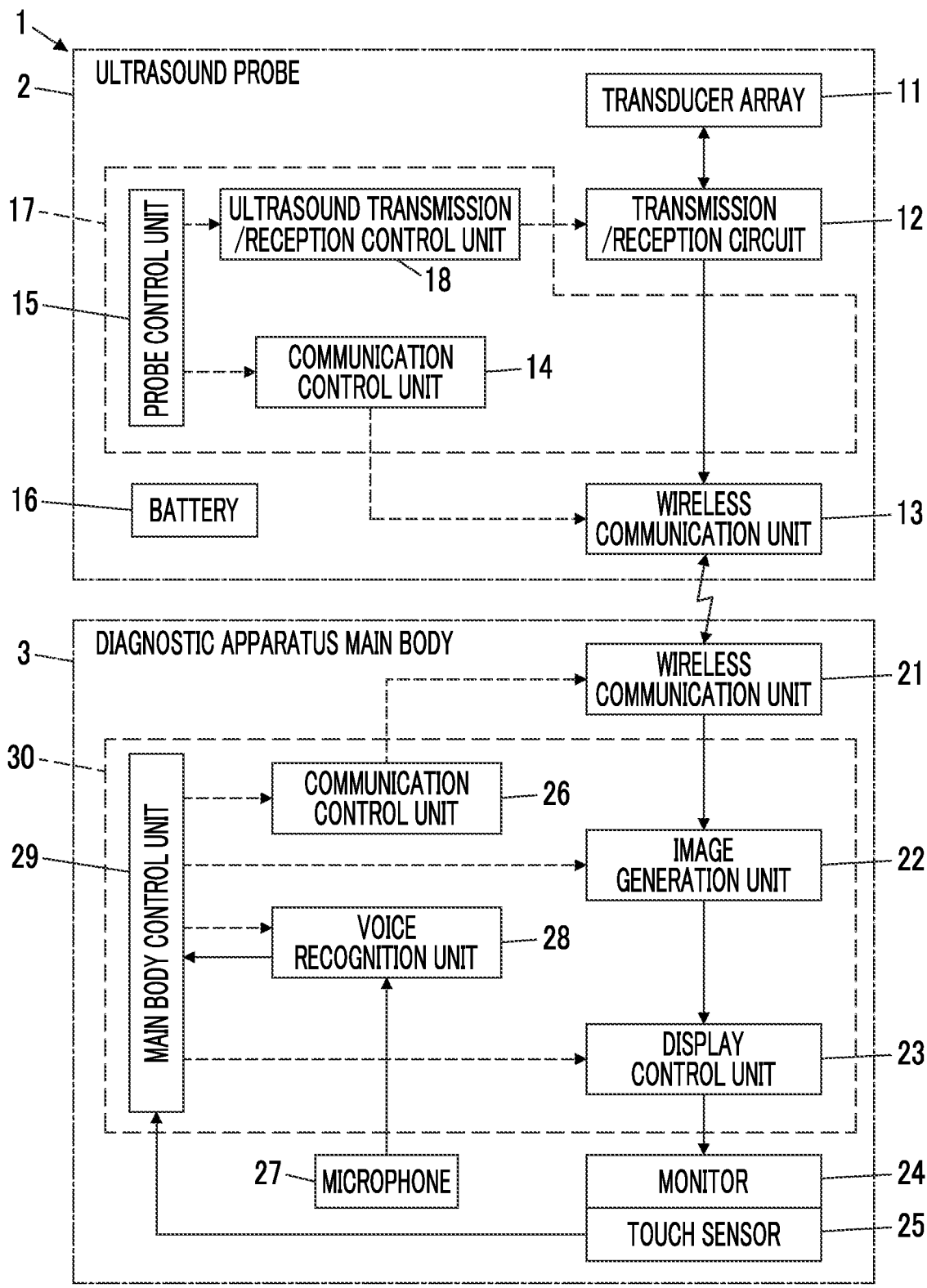
FIG. 1 is a block diagram illustrating a configuration of an ultrasound diagnostic apparatus according to an embodiment 1 of the present invention.

FIG. 1 illustrates a configuration of an ultrasound diagnostic apparatus 1 according to an embodiment 1 of the present invention. As illustrated in FIG. 1, the ultrasound diagnostic apparatus 1 is a so-called portable handheld type ultrasound diagnostic apparatus that includes an ultrasound probe 2 and a diagnostic apparatus main body 3. The ultrasound probe 2 and the diagnostic apparatus main body 3 are connected to each other by wireless communication.

The ultrasound probe 2 includes a transducer array 11, and a transmission/reception circuit 12 and a wireless communication unit 13 are sequentially connected to the transducer array 11. In addition, a communication control unit 14 is connected to the wireless communication unit 13. In addition, an ultrasound transmission/reception control unit 18 is connected to the transmission/reception circuit 12. In addition, a probe control unit 15 is connected to the communication control unit 14 and the ultrasound transmission/reception control unit 18. In addition, the ultrasound probe 2 includes a battery 16 therein. Further, a probe-side processor 17 is configured by the communication control unit 14, the probe control unit 15, and the ultrasound transmission/reception control unit 18.

The diagnostic apparatus main body 3 includes a wireless communication unit 21, and an image generation unit 22, a display control unit 23, and a monitor 24 are sequentially connected to the wireless communication unit 21. In addition, a touch sensor 25 is disposed by being superimposed on the monitor 24. In addition, a communication control unit 26 is connected to the wireless communication unit 21. In addition, the diagnostic apparatus main body 3 includes a microphone 27, and a voice recognition unit 28 is connected to the microphone 27. In addition, a main body control unit 29 is connected to the image generation unit 22, the display control unit 23, the touch sensor 25, the communication control unit 26, and the voice recognition unit 28.

Further, a main-body-side processor 30 for the ultrasound diagnostic apparatus 1 is configured by the image generation unit 22, the display control unit 23, the communication control unit 26, the voice recognition unit 28, and the main body control unit 29.

The transducer array 11 of the ultrasound probe 2 includes a plurality of ultrasound transducers which are one-dimensionally or two-dimensionally arranged. Each of these transducers transmits an ultrasound wave according to a drive signal supplied from the transmission/reception circuit 12, receives a reflected wave from a subject, and outputs a reception signal. Each transducer is configured by, for example, forming electrodes on both ends of a piezoelectric body such as a piezoelectric ceramic represented by lead zirconate titanate (PZT), a polymeric piezoelectric element represented by poly vinylidene di fluoride (PVDF), or a piezoelectric single crystal represented by lead magnesium niobate-lead titanate (PMN-PT).

Figure 2:
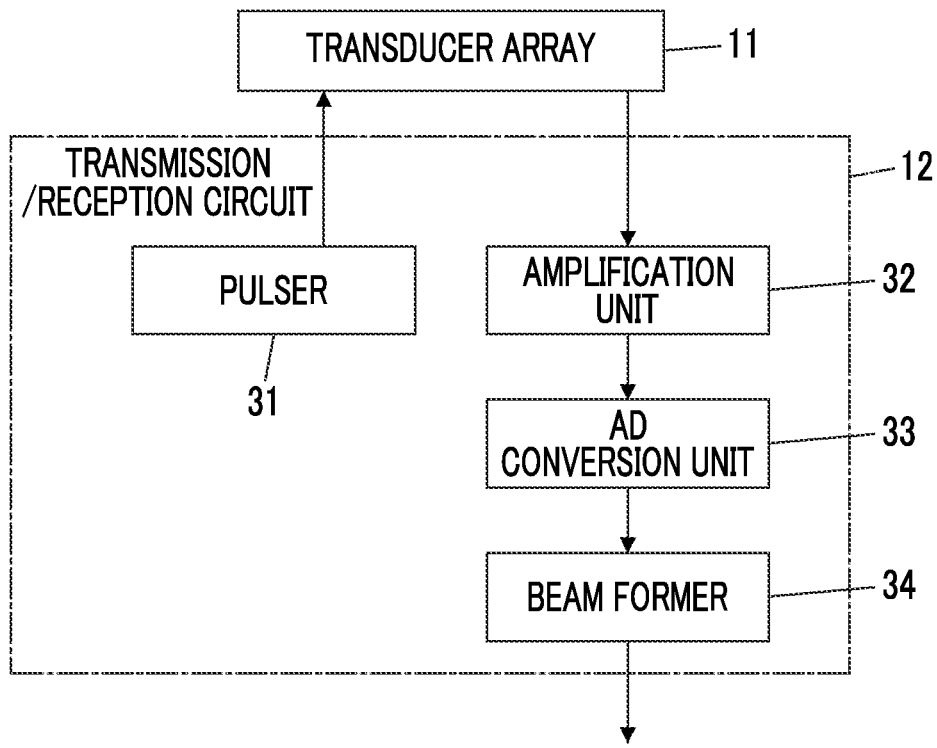
FIG. 2 is a block diagram illustrating an internal configuration of a transmission/reception circuit according to the embodiment 1 of the present invention.

The transmission/reception circuit 12 transmits an ultrasound wave from the transducer array 11 and generates a sound ray signal based on the reception signal acquired by the transducer array 11 under a control of the probe control unit 15. As illustrated in FIG. 2, the transmission/reception circuit 12 includes a pulser 31 connected to the transducer array 11, an amplification unit 32 connected in series from the transducer array 11, an analog-to-digital (AD) conversion unit 33, and a beam former 34.

The pulser 31 includes, for example, a plurality of pulse generators, adjusts a delay amount of each drive signal based on a transmission delay pattern which is selected according to a control signal from the probe control unit 15 such that ultrasound waves to be transmitted from the plurality of transducers of the transducer array 11 form ultrasound beams, and supplies each drive signal with the adjusted delay amount to the plurality of transducers. In this way, in a case where a voltage having a pulse shape or a continuous wave shape is applied to the electrodes of the transducers of the transducer array 11, the piezoelectric body expands and contracts. Thereby, ultrasound waves having a pulse shape or a continuous wave shape are generated from each transducer, and thus an ultrasound beam is formed from a composite wave of these ultrasound waves.

The transmitted ultrasound beam is reflected by an object such as a portion of a subject, and an ultrasound echo propagates toward the transducer array 11 of the ultrasound probe 2. The ultrasound echo which propagates toward the transducer array 11 in this way is received by each transducer included in the transducer array 11. At this time, in a case where the propagating ultrasound echo is received, each transducer included in the transducer array 11 expands and contracts. Thereby, a reception signal as an electrical signal is generated, and these reception signals are output to the amplification unit 32.

The amplification unit 32 amplifies the signal which is input from each transducer included in the transducer array 11, and transmits the amplified signal to the AD conversion unit 33. The AD conversion unit 33 converts the signal transmitted from the amplification unit 32 into pieces of digital reception data, and transmits the pieces of reception data to the beam former 34. The beam former 34 performs so-called reception focus processing by applying and adding a delay to each of the pieces of reception data which is converted by the AD conversion unit 33 according to a sound velocity or a sound velocity distribution which is set based on a reception delay pattern selected according to a control signal from the probe control unit 15. By this reception focus processing, a sound ray signal obtained by performing phasing addition on each of the pieces of reception data which is converted by the AD conversion unit 33 and narrowing down a focus of the ultrasound echo is acquired.

The ultrasound transmission/reception control unit 18 controls transmission of the ultrasound beam and reception of the ultrasound echo by the ultrasound probe 2 by controlling the transmission/reception circuit 12 according to an instruction from the probe control unit 15. The ultrasound transmission/reception control unit 18 changes a position of a transmission focus of the ultrasound beam, for example, based on an instruction from the probe control unit 15.

The wireless communication unit 13 of the ultrasound probe 2 is configured by a circuit and the like including an antenna for transmitting and receiving radio waves, and performs wireless communication with the wireless communication unit 21 of the diagnostic apparatus main body 3. At this time, the wireless communication unit 13 of the ultrasound probe 2 generates a transmission signal representing the sound ray signal by modulating carriers based on the sound ray signal generated by the transmission/reception circuit 12, and wirelessly transmits the generated transmission signal to the wireless communication unit 21 of the diagnostic apparatus main body 3. As the carrier modulation method, for example, amplitude shift keying (ASK), phase shift keying (PSK), quadrature phase shift keying (QPSK), 16 quadrature amplitude modulation (16 QAM), or the like is used.

The probe control unit 15 controls each unit of the ultrasound probe 2 based on a program or the like stored in advance. In addition, the probe control unit 15 can transmit the ultrasound beam and receive the ultrasound echo according to any one of a plurality of examination modes by controlling the transmission/reception circuit 12. Here, the examination mode indicates any one of examination modes that can be used in the ultrasound diagnostic apparatus 1, such as a B (brightness) mode, an M (motion) mode, a CD (color doppler) mode, a PD (power doppler) mode, a PW (pulse doppler) mode, or a CW (continuous wave doppler) mode.

The communication control unit 14 controls the wireless communication unit 13 of the ultrasound probe 2 such that the sound ray signal is transmitted at a transmission radio wave strength which is set by the probe control unit 15.

The battery 16 is included in the ultrasound probe 2, and supplies power to each circuit of the ultrasound probe 2.

The wireless communication unit 21 of the diagnostic apparatus main body 3 is configured by a circuit and the like including an antenna for transmitting and receiving radio waves, and performs wireless communication with the wireless communication unit 13 of the ultrasound probe 2. At this time, the wireless communication unit 21 of the diagnostic apparatus main body 3 receives, for example, the transmission signal representing a sound ray signal which is wirelessly transmitted from the wireless communication unit 13 of the ultrasound probe 2 via the antenna, demodulates the received transmission signal, and outputs the sound ray signal.

The communication control unit 26 of the main-body-side processor 30 controls the wireless communication unit 21 of the diagnostic apparatus main body 3 such that the transmission signal is received from the wireless communication unit 13 of the ultrasound probe 2.

Figure 3:
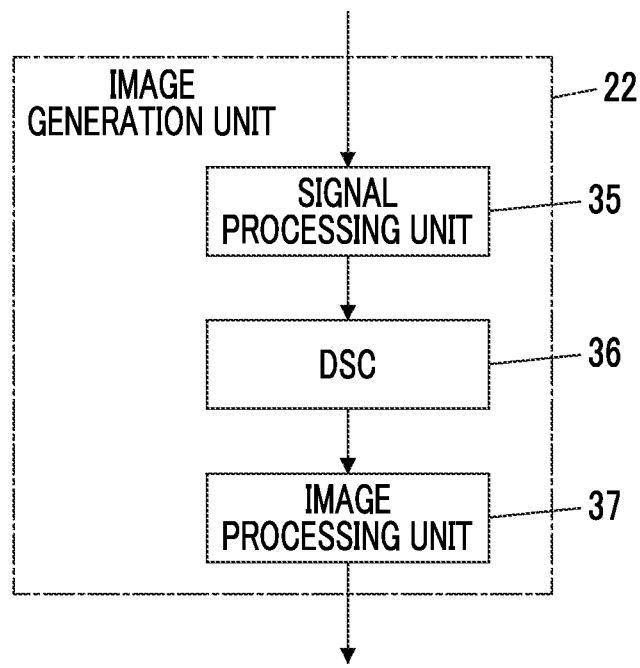
FIG. 3 is a block diagram illustrating an internal configuration of an image generation unit according to the embodiment 1 of the present invention.

As illustrated in FIG. 3, the image generation unit 22 has a configuration in which a signal processing unit 35, a digital scan converter (DSC) 36, and an image processing unit 37 are connected in series.

The signal processing unit 35 generates a B mode image signal, which is tomographic image information related to tissues in the subject, by performing correction of attenuation due to a distance according to a depth of a reflection position of the ultrasound wave and then performing envelope detection processing, on the sound ray signal which is generated by the beam former 34 of the transmission/reception circuit 12 and is received by the wireless communication unit 21.

The DSC 36 converts (raster-converts) the B mode image signal generated by the signal processing unit 35 into an image signal conforming to a normal television signal scanning method.

The image processing unit 37 performs required various image processing such as gradation processing on the B mode image signal which is input from the DSC 36, and then outputs the B mode image signal to the display control unit 23. In the following, the B mode image signal obtained by performing image processing by the image processing unit 37 is simply referred to as an ultrasound image.

Under a control of the main body control unit 29, the display control unit 23 displays the ultrasound image on the monitor 24 by performing predetermined processing on the ultrasound image generated by the image generation unit 22. Further, the display control unit 23 displays, on the monitor 24, an operation panel or the like for allowing a user to perform an input operation, in addition to the ultrasound image.

The monitor 24 displays the ultrasound image and the like, and includes a display device such as a liquid crystal display (LCD) or an organic electroluminescence (EL) display.

The touch sensor 25 is disposed by being superimposed on the display screen of the monitor 24, and allows a user to perform an input operation by a so-called touch operation by bringing a finger, a stylus pen, or the like into contact with or into close to the display screen of the monitor 24. Information which is input by the user via the touch sensor 25 is transmitted to the main body control unit 29.

The microphone 27 is attached to the diagnostic apparatus main body 3, and is for inputting a voice of a user.

The voice recognition unit 28 recognizes a voice of a user that is input via the microphone 27. For example, the voice recognition unit 28 recognizes a voice of a user, and generates voice recognition information as a text string or the like. The voice recognition information generated in this way is transmitted to the main body control unit 29.

The main body control unit 29 controls each unit of the diagnostic apparatus main body 3 based on the program stored in advance, the input operation of the user via the touch sensor 25, and voice recognition information from the voice recognition unit 28.

Figure 4:
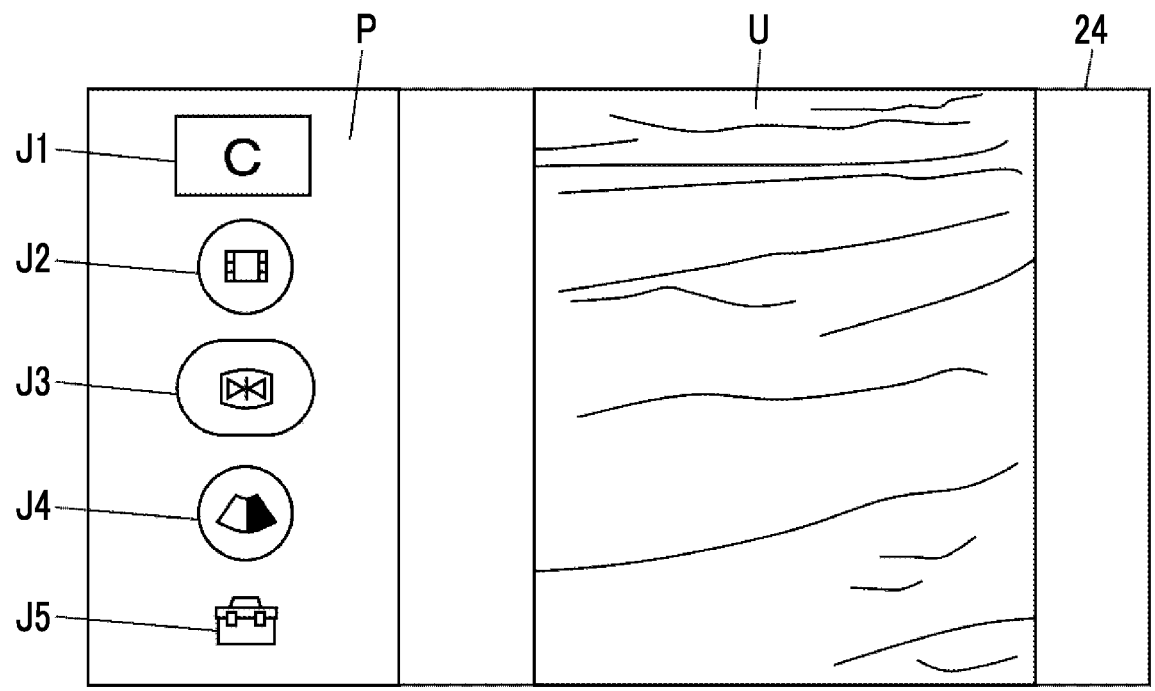
FIG. 4 is a diagram schematically illustrating a display example of a monitor in a case of a normal screen display mode according to the embodiment 1 of the present invention.
Figure 5:
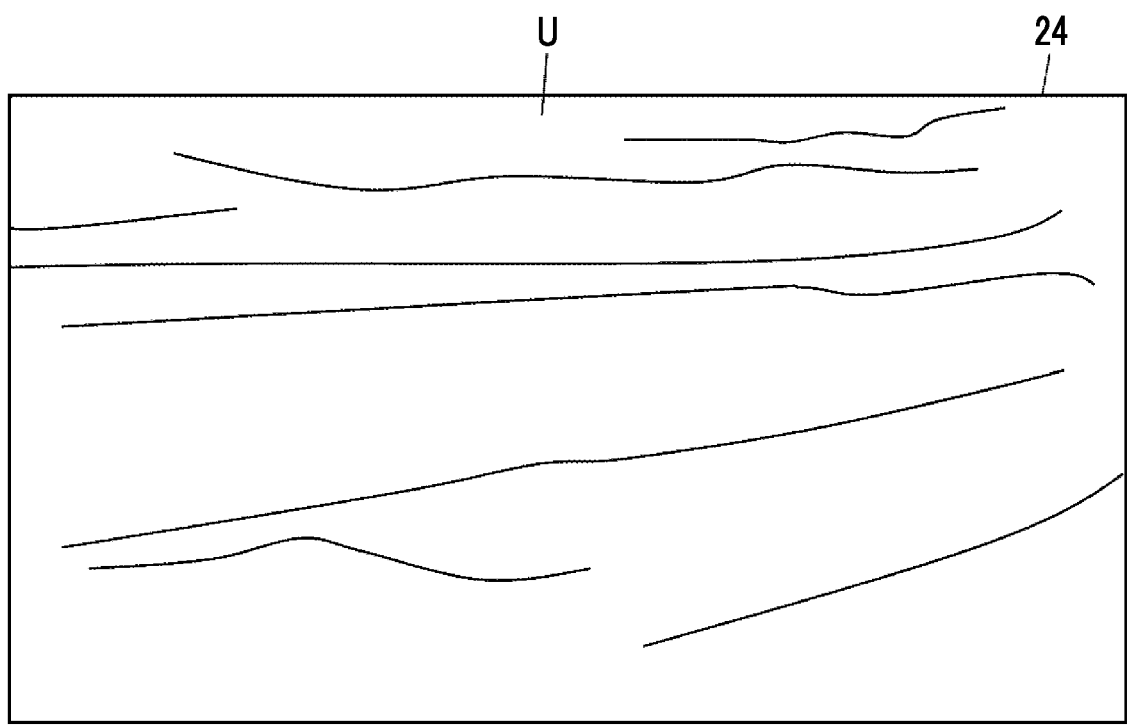
FIG. 5 is a diagram schematically illustrating a display example of a monitor in a case of a full-screen display mode according to the embodiment 1 of the present invention.

In particular, based on the input operation of the user via the touch sensor 25 or based on voice recognition performed on the voice of the user that is input via the microphone 27 by the voice recognition unit 28, the main body control unit 29 performs mode switching between a normal screen display mode in which normal screen display illustrated in FIG. 4 is performed on the monitor 24 and a full-screen display mode in which full-screen display illustrated in FIG. 5 is performed on the monitor 24 and an operation of the ultrasound diagnostic apparatus 1 by the voice via the microphone 27 is possible.

The normal screen display mode is, as illustrated in FIG. 4, a mode in which normal screen display including an ultrasound image U generated by the image generation unit 22 and an operation panel P for operating the ultrasound diagnostic apparatus 1 is performed on the monitor 24. The operation panel P includes a plurality of operation icons J1 to J5 for causing the ultrasound diagnostic apparatus 1 to perform a predetermined operation. In a case where any one of the plurality of operation icons J1 to J5 is touched by the user, an operation corresponding to the any one of the touched operation icons J1 to J5 is performed.

For example, the operation icon J1 is for switching the examination mode, and the operation icon J2 is for storing the ultrasound images U including a plurality of frames continuously generated within a certain time period. The operation icon J3 is for freeze-displaying the ultrasound image U on the monitor 24, the operation icon J4 is for changing a so-called gain and a depth, and the operation icon J5 is for displaying a plurality of other operation icons on the monitor 24.

The full-screen display mode is, for example, as illustrated in FIG. 5, a mode in which the operation of the ultrasound diagnostic apparatus 1 is performed by the voice of the user via the microphone 27 while performing a full-screen display in which the operation panel P and the mark M are not displayed and the ultrasound image U is enlarged and displayed on the entire display screen of the monitor 24.

Here, each of the probe-side processor 17 in the ultrasound probe 2 and the main-body-side processor 30 in the diagnostic apparatus main body 3 is configured with a central processing unit (CPU) and a control program for causing the CPU to perform various processing, the probe-side processor 17 including the communication control unit 14, the probe control unit 15, and the ultrasound transmission/reception control unit 18, and the main-body-side processor 30 including the image generation unit 22, the display control unit 23, the communication control unit 26, the voice recognition unit 28, and the main body control unit 29. On the other hand, each of the probe-side processor 17 and the main-body-side processor 30 may be configured by using a field programmable gate array (FPGA), a digital signal processor (DSP), an application specific integrated circuit (ASIC), a graphics processing unit (GPU), or other integrated circuits (IC), or may be configured by using a combination thereof.

In addition, the communication control unit 14, the probe control unit 15, and the ultrasound transmission/reception control unit 18 of the probe-side processor 17 can be partially or wholly integrated into one CPU or the like. In addition, the image generation unit 22, the display control unit 23, the communication control unit 26, the voice recognition unit 28, and the main body control unit 29 of the main-body-side processor 30 can also be partially or wholly integrated into one CPU or the like.

Figure 6:
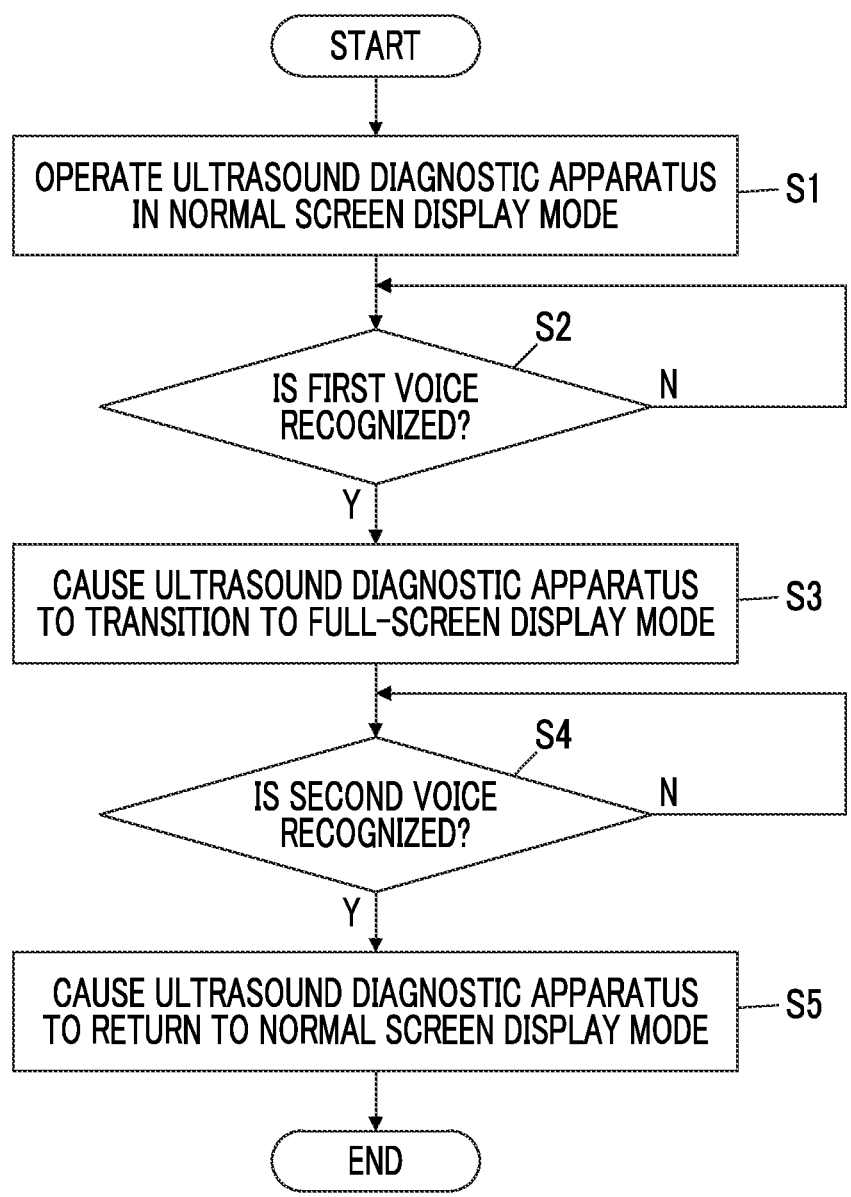
FIG. 6 is a flowchart illustrating an operation of the ultrasound diagnostic apparatus according to the embodiment 1 of the present invention.

Next, an operation in a case where the ultrasound diagnostic apparatus 1 according to the embodiment 1 of the present invention performs switching between the normal screen display mode and the full-screen display mode will be described using a flowchart of FIG. 6. Here, as a switching operation between the normal screen display mode and the full-screen display mode, an example of inputting a voice of the user via the microphone 27 will be introduced.

First, in a case where ultrasound diagnosis of a subject is started by an input operation or the like of a user via the touch sensor 25, in step S1, the main body control unit 29 operates the ultrasound diagnostic apparatus 1 in the normal screen display mode. At this time, normal screen display as illustrated in FIG. 4 is performed on the monitor 24.

In step S2, the main body control unit 29 determines whether or not a specific first voice such as "Transition to the voice recognition mode" is recognized by the voice recognition unit 28. At this time, the voice recognition unit 28 generates, for example, voice recognition information as a text string or the like by recognizing the voice of the user. The main body control unit 29 determines whether or not the voice recognition information generated by the voice recognition unit 28 corresponds to the first voice. In a case where the voice recognition information corresponds to the first voice, the main body control unit 29 determines that the first voice is recognized by the voice recognition unit 28. In addition, in a case where the voice recognition information does not correspond to the first voice, the main body control unit 29 determines that the first voice is not recognized by the voice recognition unit 28.

Here, in a case where it is determined that the first voice is not recognized, the determination in step S2 is performed again. In this way, the operation in the normal screen display mode is maintained until it is determined that the first voice is recognized.

In step S2, in a case where it is determined that the first voice is recognized, the process proceeds to step S3.

In step S3, the main body control unit 29 causes the ultrasound diagnostic apparatus 1 to transition from the normal screen display mode to the full-screen display mode. At this time, a full-screen display as illustrated in FIG. 5 is performed on the monitor 24. Thereby, for example, even in a case where a size of the monitor 24 is small and thus it is difficult for the user to confirm the ultrasound image U displayed on the monitor 24 in detail in the normal screen display, the ultrasound image U is enlarged and displayed on the entire display screen of the monitor 24, and thus the user can confirm the ultrasound image U in detail.

In addition, the main body control unit 29 analyzes the voice recognition information generated by the voice recognition unit 28 based on the voice of the user that is input via the microphone 27, and controls the ultrasound diagnostic apparatus 1 such that an operation corresponding to the voice recognition information is performed.

Subsequently, in step S4, the main body control unit 29 determines whether or not the voice recognition unit 28 recognizes a specific second voice such as "Transition to the normal screen display mode" by using the same method as the determination in step S2. In a case where it is determined in step S4 that the second voice is not recognized, the determination in step S4 is performed again. In this way, the operation in the full-screen display mode is maintained until it is determined that the second voice is recognized.

In step S4, in a case where it is determined that the second voice is recognized, the process proceeds to step S5.

In step S5, the main body control unit 29 causes the ultrasound diagnostic apparatus 1 to return to the full-screen display mode.

In this way, the operation of performing switching between the normal screen display mode and the full-screen display mode is completed.

On the other hand, for example, in a medical site at a remote place away from a hospital, such as a site for home nursing, a so-called handheld type ultrasound diagnostic apparatus including an ultrasound probe and a portable diagnostic apparatus main body connected to the ultrasound probe may be used. In such a handheld type ultrasound diagnostic apparatus, the diagnostic apparatus main body often includes a monitor with a touch sensor. Such a monitor has a small size in many cases, and it is necessary to display a user interface for allowing a user to perform an input operation on the monitor in addition to the captured ultrasound image. For this reason, it may be difficult for the user to confirm the ultrasound image displayed on the monitor, and it may be difficult to smoothly perform ultrasound diagnosis.

In the ultrasound diagnostic apparatus 1 according to the embodiment 1 of the present invention, even in a case where both hands of the user are not available during an examination of a subject, it is possible to easily operate the ultrasound diagnostic apparatus 1 by voice recognition. Further, the ultrasound diagnostic apparatus 1 is caused to transition from the normal screen display mode to the full-screen display mode in which the ultrasound image U is enlarged and displayed on the entire display screen of the monitor 24. Thereby, even in a case where the size of the monitor 24 is small, the user can confirm the ultrasound image U in detail. Therefore, the user can smoothly perform ultrasound diagnosis.

In the ultrasound diagnostic apparatus 1, the image generation unit 22 is included in the main-body-side processor 30 of the diagnostic apparatus main body 3. On the other hand, the image generation unit 22 may be included in the probe-side processor 17 of the ultrasound probe 2. In this case, an ultrasound image U is generated in the ultrasound probe 2, and the generated ultrasound image U is wirelessly transmitted from the ultrasound probe 2 to the diagnostic apparatus main body 3. On the other hand, the ultrasound image U is displayed on the monitor 24 in the same manner as in the case where the image generation unit 22 is included in the main-body-side processor 30 of the diagnostic apparatus main body 3.

Further, the ultrasound probe 2 and the diagnostic apparatus main body 3 are connected to each other by wireless communication. On the other hand, the communication is not limited to wireless communication, and the ultrasound probe 2 and the diagnostic apparatus main body 3 can also be connected to each other by so-called wired communication.

Further, in the full-screen display mode, the main body control unit 29 controls the ultrasound diagnostic apparatus 1 such that an operation is performed according to the voice of the user that is recognized by the voice recognition unit 28. On the other hand, for example, in a case where a list in which the voice recognized by the voice recognition unit 28 and the operation of the ultrasound diagnostic apparatus 1 are associated with each other is stored in advance, the ultrasound diagnostic apparatus 1 can be controlled based on the list. For example, in a case where the voice recognition unit 28 recognizes any voice of "freeze", "pause", and "stop", the main body control unit 29 freeze-displays the ultrasound image U on the monitor 24. In a case where the voice recognition unit 28 recognizes any voice of "moving image", "movie", and "clip", the main body control unit 29 can store the ultrasound images U including a plurality of frames generated up to a timing when a certain time is elapsed from the present.

In step S2 and step S3, the ultrasound diagnostic apparatus 1 is caused to transition from the normal screen display mode to the full-screen display mode by being triggered by recognition of the first voice. On the other hand, the trigger for the transition from the normal screen display mode to the full-screen display mode is not limited to recognition of the first voice. For example, a touch operation such as a so-called double tap in which the monitor 24 is tapped twice in a row may be set as a trigger.

On the other hand, in a case where the ultrasound diagnostic apparatus 1 is caused to transition from the normal screen display mode to the full-screen display mode by being triggered by recognition of the first voice, the user can cause the ultrasound diagnostic apparatus 1 to transition to the full-screen display mode without using a hand. Therefore, in a case where both hands of the user are not available, it is particularly useful to use the recognition of the first voice as a trigger for the transition to the full-screen display mode.

In addition, in the full-screen display mode, a touch operation of the user via the touch sensor 25 can be disabled. In this case, in the full-screen display mode, only an operation of the ultrasound diagnostic apparatus 1 by voice recognition is possible. Thus, it is possible to prevent an operation that is unintended by the user from being performed even in a case where the user mistakenly touches the display screen of the monitor 24.

Further, in the full-screen display mode, the ultrasound image U is enlarged and displayed on the entire display screen of the monitor 24. On the other hand, in a case where the ultrasound image U is enlarged, a depth position on the display screen of the monitor 24 that corresponds to a transmission focus of the ultrasound beam or a reception focus of the ultrasound echo may not fit within the display screen.

For this reason, in order to move the depth position corresponding to the transmission focus of the ultrasound beam or the reception focus of the ultrasound echo within the display screen of the monitor 24, the ultrasound transmission/reception control unit 18 can change the position of the transmission focus of the ultrasound beam according to a depth position that is a display depth of a deepest portion of the ultrasound image U displayed on the monitor 24. At this time, for example, display depth information is transmitted from the diagnostic apparatus main body 3 to the probe control unit 15 via the wireless communication unit 13, and the probe control unit 15 instructs the ultrasound transmission/reception control unit 18 to change the position of the transmission focus of the ultrasound beam based on the display depth information.

Here, generally, in a case where the user intends to observe an observation target in the ultrasound image U, in many cases, a position of the ultrasound probe is adjusted such that the observation target is positioned at the center of the ultrasound image U for ease of observation. Therefore, the ultrasound transmission/reception control unit 18 can change the position of the transmission focus of the ultrasound beam, for example, such that a position of approximately half of the display depth of the ultrasound image U displayed on the monitor 24 in the full-screen display mode is set as a depth position of the focus. Here, the approximately half of the display depth of the ultrasound image U displayed on the monitor 24 in the full-screen display mode refers to a value in a range of −5% to +5% with respect to the depth position of the half of the display depth of the ultrasound image U displayed on the monitor 24 in the full-screen display mode.

As a specific example, for example, in a case where the display depth of the ultrasound image U displayed on the monitor 24 in the normal screen display mode is 4.0 cm, where the depth position of the focus is 2.0 cm, and where the display depth of the ultrasound image U displayed on the monitor 24 in the full-screen display mode is 1.7 cm, the ultrasound transmission/reception control unit 18 can change the position of the transmission focus of the ultrasound beam such that the position of the focus is 0.8 cm.

The depth position of the focus that is changed by the ultrasound transmission/reception control unit 18 is not particularly limited to the half of the display depth of the ultrasound image U displayed on the monitor 24 in the full-screen display mode. For example, in the ultrasound image U displayed on the monitor 24 in the full-screen display mode, the depth position of the focus may be changed to a depth position corresponding to ¼ of the display depth of the ultrasound image U, or may be changed to a depth position corresponding to ⅔ of the display depth of the ultrasound image U.

In addition, in step S4 and step S5, the ultrasound diagnostic apparatus 1 is caused to transition from the full-screen display mode to the normal screen display mode by being triggered by recognition of the second voice. On the other hand, the trigger for the transition from the full-screen display mode to the normal screen display mode is not limited to recognition of the second voice. For example, a touch operation such as a double tap may be set as a trigger.

On the other hand, in a case where the ultrasound diagnostic apparatus 1 is caused to transition from the full-screen display mode to the normal screen display mode by being triggered by recognition of the second voice, the user can cause the ultrasound diagnostic apparatus 1 to transition to the normal screen display mode without using a hand. Therefore, in a case where both hands of the user are not available, it is particularly useful to use the recognition of the second voice as a trigger for the transition to the normal screen display mode.

In addition, an operation corresponding to a touch operation in the normal screen display mode and an operation corresponding to a touch operation in the full-screen display mode can be made different from each other.

For example, in a case where a so-called single tap of tapping the display screen of the monitor 24 only once is performed on the ultrasound image U in the normal screen display mode, an operation of enlarging the ultrasound image U centering on a position where the single tap is performed and displaying the enlarged ultrasound image U on the monitor 24 can be performed. On the other hand, in a case where a single tap is performed in the full-screen display mode, an operation of storing the ultrasound image U displayed on the monitor 24 can be performed.

In addition, for example, in a case where a double tap is performed in the normal screen display mode, an operation of causing the ultrasound diagnostic apparatus 1 to transition from the normal screen display mode to the full-screen display mode is performed. On the other hand, in a case where a double tap is performed in the full-screen display mode, an operation of storing the ultrasound images U including a plurality of frames generated within a certain period of time for which a certain time is elapsed from the present can be performed.

In this way, an operation corresponding to a touch operation in the normal screen display mode and an operation corresponding to a touch operation in the full-screen display mode can be made different from each other. Thereby, the user can more smoothly perform ultrasound diagnosis.

Embodiment 2

In the embodiment 1, as the switching operation between the normal screen display mode and the full-screen display mode, recognition of the first voice by the voice recognition unit 28, recognition of the second voice by the voice recognition unit 28, or a touch operation via the touch sensor 25 is used. On the other hand, the switching operation is not limited thereto.

Figure 7:
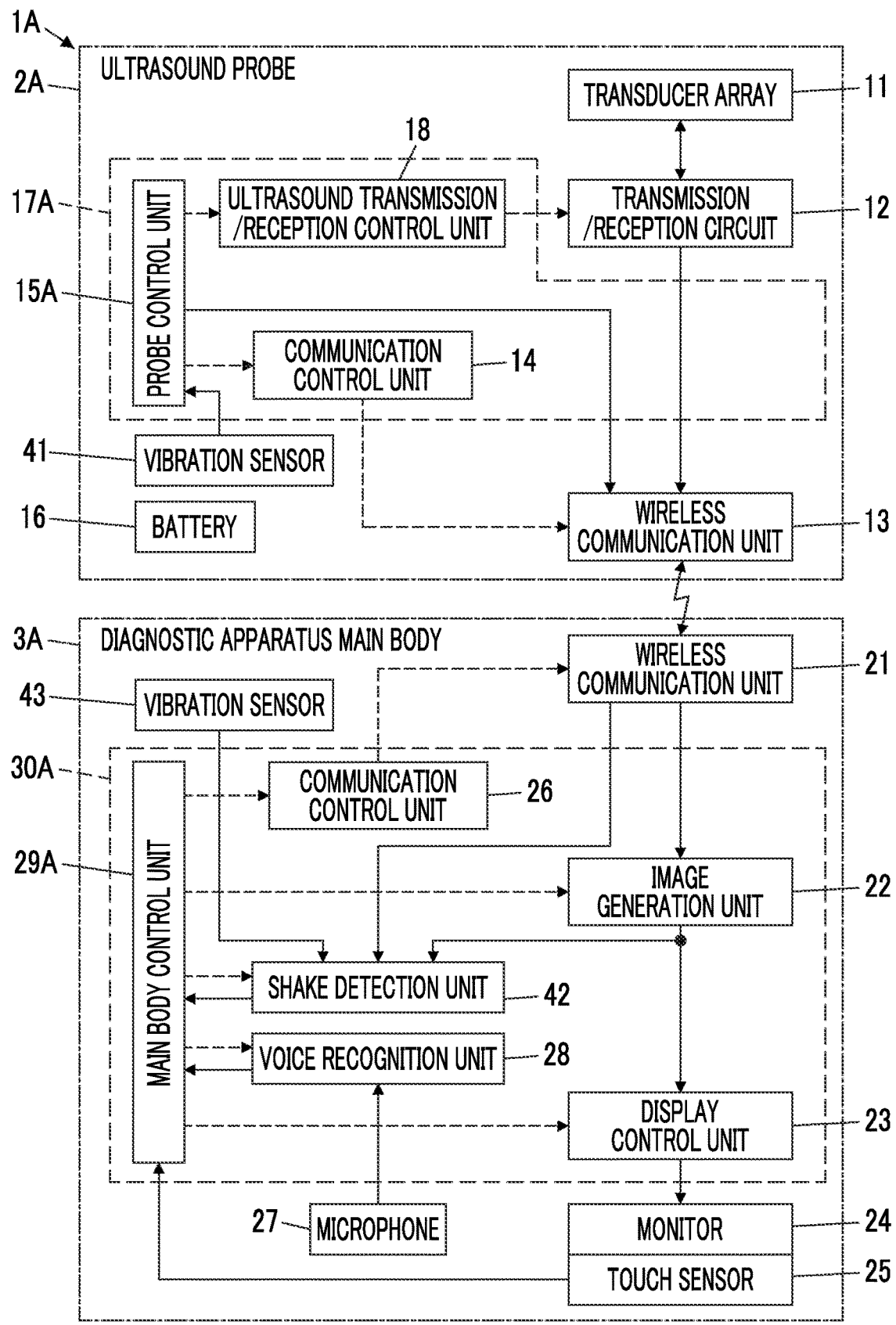
FIG. 7 is a block diagram illustrating a configuration of an ultrasound diagnostic apparatus according to an embodiment 2 of the present invention.

FIG. 7 illustrates a configuration of an ultrasound diagnostic apparatus 1A according to an embodiment 2 of the present invention. The ultrasound diagnostic apparatus 1A according to the embodiment 2 includes an ultrasound probe 2A and a diagnostic apparatus main body 3A, instead of the ultrasound probe 2 and the diagnostic apparatus main body 3 in the ultrasound diagnostic apparatus 1 according to the embodiment 1 illustrated in FIG. 1.

In the ultrasound probe 2A, as compared with the ultrasound probe 2 according to the embodiment 1, a vibration sensor 41 is added, and a probe control unit 15A is included instead of the probe control unit 15. The vibration sensor 41 is connected to the probe control unit 15A. In addition, the probe control unit 15A is connected to the wireless communication unit 13. In addition, a probe-side processor 17A is configured by the communication control unit 14, the probe control unit 15A, and the ultrasound transmission/reception control unit 18.

In the diagnostic apparatus main body 3A, as compared with the diagnostic apparatus main body 3 according to the embodiment 1, a shake detection unit 42 and a vibration sensor 43 are added, and a main body control unit 29A is included instead of the main body control unit 29. The shake detection unit 42 is connected to the wireless communication unit 21, the image generation unit 22, and the main body control unit 29A. In addition, the vibration sensor 43 is connected to the shake detection unit 42. In addition, a main-body-side processor 30A is configured by the image generation unit 22, the display control unit 23, the communication control unit 26, the voice recognition unit 28, the main body control unit 29A, and the shake detection unit 42.

The vibration sensor 41 of the ultrasound probe 2A includes a gyro sensor, an acceleration sensor, or the like, and is a sensor that detects a vibration of the ultrasound probe 2A. A signal indicating that a vibration of the ultrasound probe 2A is detected by the vibration sensor 41 is transmitted to the wireless communication unit 13 via the probe control unit 15A, and is transmitted from the wireless communication unit 13 to the diagnostic apparatus main body 3A. Further, the signal is transmitted from the wireless communication unit 21 of the diagnostic apparatus main body 3A to the shake detection unit 42.

In addition, similar to the vibration sensor 41 of the ultrasound probe 2A, the vibration sensor 43 of the diagnostic apparatus main body 3A includes a gyro sensor, an acceleration sensor, or the like, and is a sensor that detects a vibration of the diagnostic apparatus main body 3A. A signal indicating that a vibration of the diagnostic apparatus main body 3A is detected by the vibration sensor 43 is transmitted to the shake detection unit 42.

The shake detection unit 42 detects that the ultrasound probe 2A is shaken by the user based on the signal received from the vibration sensor 41 of the ultrasound probe 2A. In addition, the shake detection unit 42 can detect a vibration of the ultrasound probe 2A by analyzing the ultrasound images U including a plurality of frames continuously generated by the image generation unit 22, and can detect that the ultrasound probe 2A is shaken by the user.

In addition, the shake detection unit 42 detects that the diagnostic apparatus main body 3A is shaken by the user based on the signal received from the vibration sensor 43 of the diagnostic apparatus main body 3A.

In this way, in a case where the shake detection unit 42 detects that the ultrasound probe 2A or the diagnostic apparatus main body 3A is shaken by the user, the signal indicating that the ultrasound probe 2A or the diagnostic apparatus main body 3A is shaken by the user is transmitted to the main body control unit 29A.

Thereby, the main body control unit 29A can perform switching from the normal screen display mode to the full-screen display mode and switching from the full-screen display mode to the normal screen display mode by being triggered by a shake operation on the ultrasound probe 2A by the user or a shake operation on the diagnostic apparatus main body 3A by the user.

As described above, even in a case where a shake operation on the ultrasound probe 2A or a shake operation on the diagnostic apparatus main body 3A is used as a switching operation between the normal screen display mode and the full-screen display mode, similar to the embodiment 1, the user can smoothly perform ultrasound diagnosis.

In the ultrasound diagnostic apparatus 1A according to the embodiment 2, the ultrasound probe 2 includes the vibration sensor 41 and the diagnostic apparatus main body 3A includes the vibration sensor 43. On the other hand, in a case where any one of the vibration sensors 41 and 43 is included in the ultrasound diagnostic apparatus 1A, the ultrasound diagnostic apparatus 1A may be configured such that only one of a shake operation on the ultrasound probe 2A and a shake operation on the diagnostic apparatus main body 3A is performed. Even in this case, as in the case where the vibration sensors 41 and 42 are included in the ultrasound diagnostic apparatus 1A, the user can smoothly perform ultrasound diagnosis.

Embodiment 3

In the full-screen display mode, a display according to a type of the ultrasound probe 2 may be performed on the monitor 24. Here, the type of the ultrasound probe refers to a type of an ultrasound probe that is classified according to use of the ultrasound probe, such as a dedicated ultrasound probe that is used in a case where a puncture procedure is performed, a dedicated ultrasound probe for observing a blood vessel, and the like.

Figure 8:
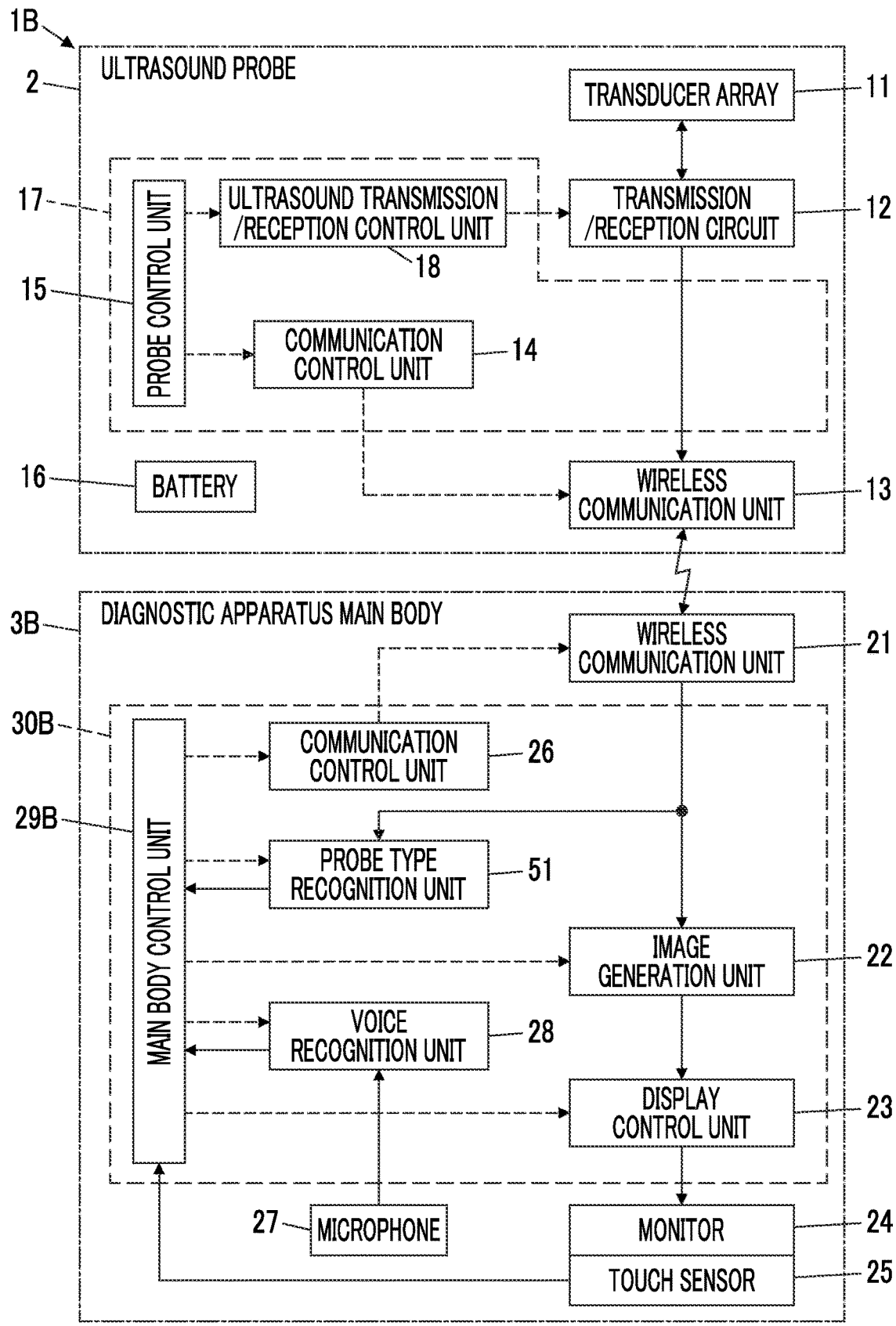
FIG. 8 is a block diagram illustrating a configuration of an ultrasound diagnostic apparatus according to an embodiment 3 of the present invention.

FIG. 8 illustrates a configuration of an ultrasound diagnostic apparatus 1B according to an embodiment 3. The ultrasound diagnostic apparatus 1B according to the embodiment 3 includes a diagnostic apparatus main body 3B instead of the diagnostic apparatus main body 3 in the ultrasound diagnostic apparatus 1 according to the embodiment 1 illustrated in FIG. 1. In the diagnostic apparatus main body 3B, as compared with the diagnostic apparatus main body 3 according to the embodiment 1, a probe type recognition unit 51 is added, and a main body control unit 29B is included instead of the main body control unit 29.

In addition, a main-body-side processor 30B is configured by the image generation unit 22, the display control unit 23, the communication control unit 26, the voice recognition unit 28, the main body control unit 29B, and the probe type recognition unit 51.

The probe type recognition unit 51 is connected to the wireless communication unit 21 and the main body control unit 29B. The probe type recognition unit 51 recognizes a type of the ultrasound probe 2 connected to the diagnostic apparatus main body 3B. The probe type recognition unit 51 stores, for example, types of a plurality of ultrasound probes in advance, receives identification information such as a model number from the ultrasound probe 2 connected to the diagnostic apparatus main body 3B, and recognizes a type of the ultrasound probe 2 based on the received identification information. Information indicating the type of the ultrasound probe 2 that is recognized by the probe type recognition unit 51 is transmitted to the main body control unit 29B.

Figure 9:
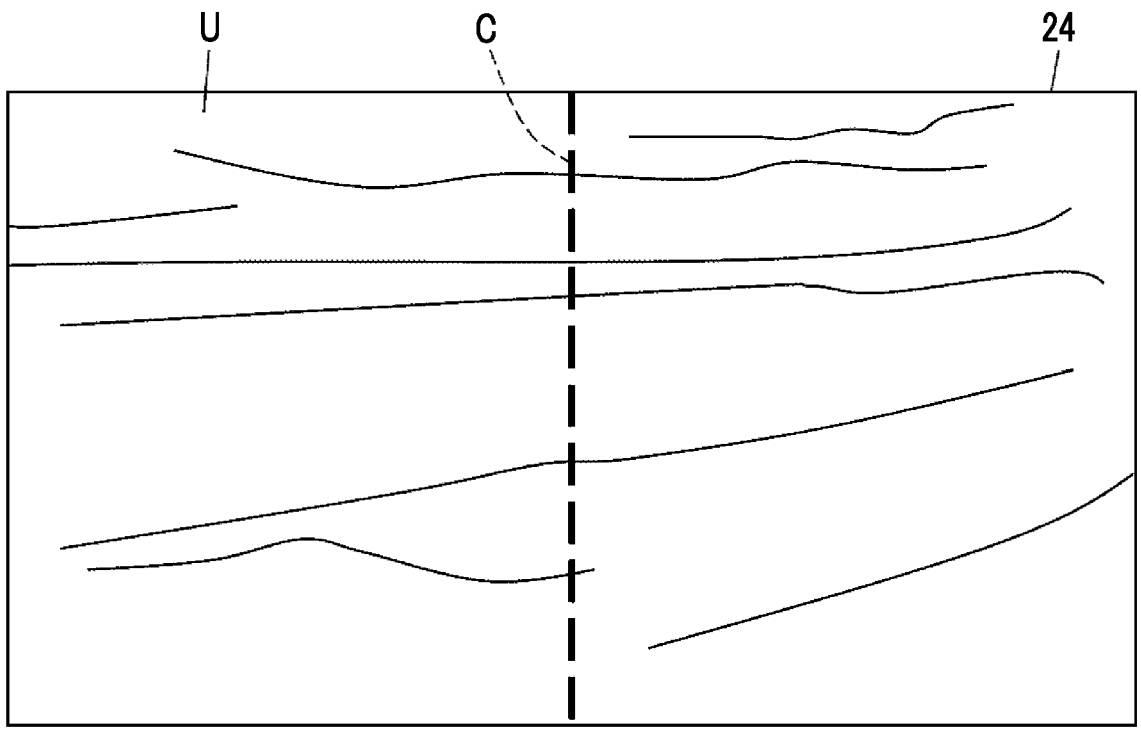
FIG. 9 is a diagram schematically illustrating a display example of a monitor in a case of a full-screen display mode according to the embodiment 3 of the present invention.

In the full-screen display mode, the main body control unit 29B performs a display according to the type of the ultrasound probe 2 that is recognized by the probe type recognition unit 51. For example, in a case where the probe type recognition unit 51 recognizes that the ultrasound probe 2 connected to the diagnostic apparatus main body 3B is a dedicated ultrasound probe which is used in a case of inserting a puncture needle into the subject, as illustrated in FIG. 9, the main body control unit 29B can superimpose a center line C, which is for assisting alignment between a tip of the puncture needle and an object such as a blood vessel into which the puncture needle is to be inserted, on the ultrasound image U and display the ultrasound image U on which the center line C is superimposed on the monitor 24.

As described above, according to the ultrasound diagnostic apparatus 1B according to the embodiment 3 of the present invention, the type of the ultrasound probe 2 connected to the diagnostic apparatus main body 3B is recognized by the probe type recognition unit 51, and a display according to the recognized type of the ultrasound probe 2 is performed on the monitor 24 in the full-screen display mode. Therefore, the user can save an effort to perform an input operation for performing the display according to the type of the ultrasound probe 2, and can more smoothly perform ultrasound diagnosis.

In a case where the probe type recognition unit 51 recognizes that the ultrasound probe 2 connected to the diagnostic apparatus main body 3B is a dedicated ultrasound probe which is used in a case of inserting a puncture needle into the subject, an example in which the center line C is displayed on the monitor 24 in the full-screen display mode has been described. On the other hand, a display form on the monitor 24 is not particularly limited thereto.

For example, it is considered a case where a blood vessel detection unit (not illustrated) that performs processing for detecting a blood vessel appearing in the ultrasound image U by analyzing the ultrasound image U generated by the image generation unit 22 is included in the diagnostic apparatus main body 3B and where the probe type recognition unit 51 recognizes that the ultrasound probe 2 connected to the diagnostic apparatus main body 3B is a dedicated ultrasound probe which is used in a case of observing a blood vessel of the subject or a dedicated ultrasound probe which is used in a case of inserting a puncture needle into a blood vessel of the subject.

In this case, in the normal screen display mode, the main body control unit 29B superimposes a highlight display for a blood vessel region on the ultrasound image U and displays the ultrasound image U on which the highlight display is superimposed on the monitor 24, such as displaying a contour line of a blood vessel region detected by the blood vessel detection unit on the monitor 24. Further, in the full-screen display mode, the highlight display for the blood vessel region may not displayed.

Embodiment 4

In the ultrasound diagnostic apparatus 1 according to the embodiment 1, the ultrasound probe 2 and the diagnostic apparatus main body 3 with the monitor 24 are directly connected to each other by wireless communication, and the diagnostic apparatus main body 3 includes the main-body-side processor 30. On the other hand, for example, a processor that controls the ultrasound diagnostic apparatus 1 may be provided on a network.

Figure 10:
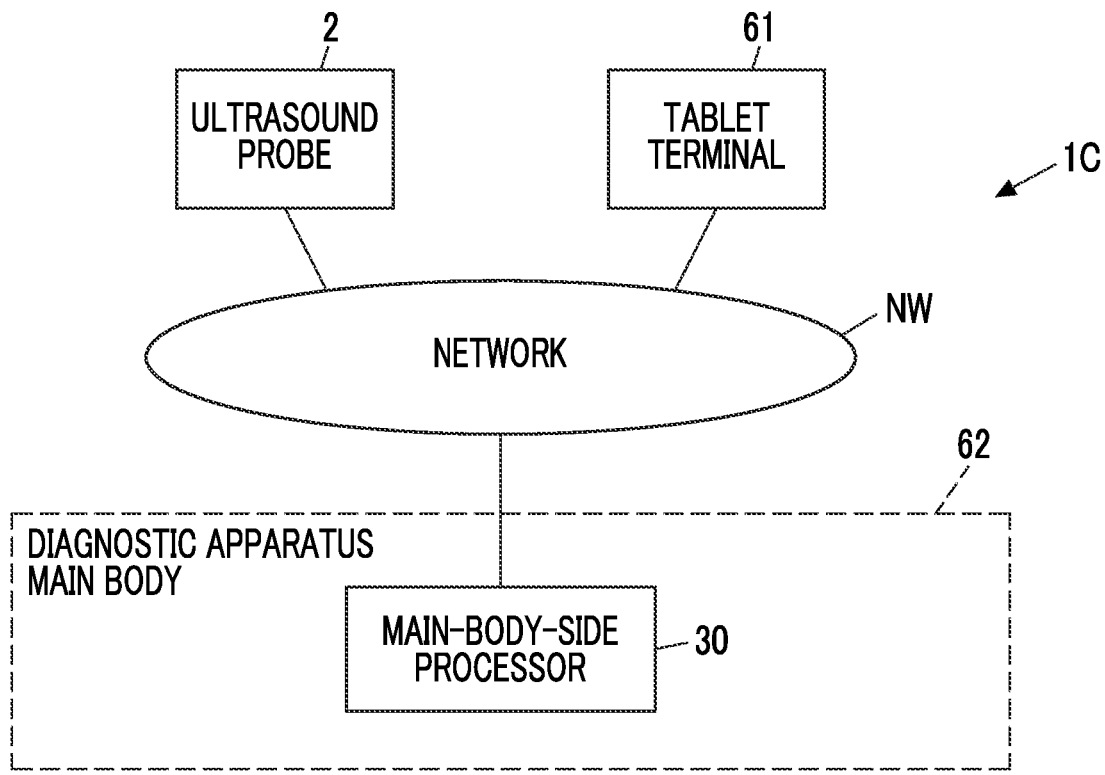
FIG. 10 is a block diagram illustrating a configuration of an ultrasound diagnostic apparatus according to an embodiment 4 of the present invention.

As illustrated in FIG. 10, in an ultrasound diagnostic apparatus 1C according to the embodiment 4, an ultrasound probe 2 and a tablet terminal 61 are connected to a diagnostic apparatus main body 62 via a network NW.

Although not illustrated, the tablet terminal 61 is a portable thin computer including a monitor 24 with a touch sensor 25 and a microphone 27, and corresponds to the diagnostic apparatus main body 3 according to the embodiment 1 illustrated in FIG. 1 from which the main-body-side processor 30 is excluded.

The diagnostic apparatus main body 62 is obtained by excluding the monitor 24, the touch sensor 25, and the microphone 27 from the diagnostic apparatus main body 3 according to the embodiment 1, and includes a main-body-side processor 30.

Even in a case where the ultrasound diagnostic apparatus 1C has such a configuration, as in the ultrasound diagnostic apparatus 1 according to the embodiment 1, switching between the normal screen display mode and the full-screen display mode can be performed based on the voice recognition by the voice recognition unit 28 or the input operation via the touch sensor 25. Further, in the full-screen display mode, the ultrasound image U is enlarged and displayed on the entire display screen of the monitor 24. Thereby, the user can smoothly perform ultrasound diagnosis.

It has been described that a form of the embodiment 4 is applied to the embodiment 1. On the other hand, the form of the embodiment 4 can be similarly applied to the embodiments 2 and 3.

EXPLANATION OF REFERENCES

1, 1A, 1B, 1C: ultrasound diagnostic apparatus
2: ultrasound probe
3, 3A, 3B, 62: diagnostic apparatus main body 11: transducer array
12: transmission/reception circuit
13, 21: wireless communication unit
14, 26: communication control unit
15, 15A: probe control unit
16: battery
17, 17A: probe-side processor
18: ultrasound transmission/reception control unit
22: image generation unit
23: display control unit
24: monitor
25: touch sensor
27: microphone
28: voice recognition unit
29, 29A, 29B: main body control unit
30, 30A, 30B: main-body-side processor
31: pulser
32: amplification unit
33: AD conversion unit
34: beam former
35: signal processing unit
36: DSC
37: image processing unit
41, 43: vibration sensor
42: shake detection unit
51: probe type recognition unit
61: tablet terminal
C: center line
J1 to J5: operation icons
M: mark
NW: network
P: operation panel
U: ultrasound image

What is claimed is:

1. A handheld type ultrasound diagnostic apparatus comprising:
  an ultrasound probe; and
  a diagnostic apparatus main body connected to the ultrasound probe,
  wherein the diagnostic apparatus main body includes
  a monitor with a touch sensor,
  a microphone configured to input a voice, and
  a processor configured to
  generate an ultrasound image based on a reception signal acquired by using the ultrasound probe,
  recognize a voice which is input via the microphone,
  perform switching between a normal screen display mode and a full-screen display mode by performing a mode switching operation on the diagnostic apparatus main body or the ultrasound probe, the normal screen display mode being a mode in which the processor is configured to display the ultrasound image and an operation panel for operating the ultrasound diagnostic apparatus on the monitor and perform an operation of the ultrasound diagnostic apparatus via the operation panel, and the full-screen display mode being a mode in which the processor is configured to display only the ultrasound image on the monitor and enable an operation of the ultrasound diagnostic apparatus by using a voice, and
  perform different operations for a specific touch operation on the ultrasound image from a user between the normal screen display mode and the full-screen display mode.

2. The ultrasound diagnostic apparatus according to claim 1,
  wherein the mode switching operation for switching from the normal screen display mode to the full-screen display mode is a touch operation on a screen of the monitor or an input operation of a predetermined first voice.

3. The ultrasound diagnostic apparatus according to claim 1,
  wherein the processor is further configured to detect a shake operation on the diagnostic apparatus main body or the ultrasound probe,
  the mode switching operation for switching from the normal screen display mode to the full-screen display mode is the shake operation.

4. The ultrasound diagnostic apparatus according to claim 3, further comprising:
  a vibration sensor configured to detect a vibration of the diagnostic apparatus main body or the ultrasound probe,
  wherein the processor is further configured to detect the shake operation based on the vibration of the diagnostic apparatus main body or the ultrasound probe that is detected by the vibration sensor.

5. The ultrasound diagnostic apparatus according to claim 3,
  wherein the processor is further configured to detect the shake operation by analyzing ultrasound images including a plurality of continuous frames.

6. The ultrasound diagnostic apparatus according to claim 2,
  wherein the mode switching operation for switching from the full-screen display mode to the normal screen display mode is a touch operation on a screen of the monitor or an input operation of a predetermined second voice different from the first voice.

7. The ultrasound diagnostic apparatus according to claim 3,
  wherein the mode switching operation for switching from the full-screen display mode to the normal screen display mode is a touch operation on a screen of the monitor or an input operation of a predetermined second voice different from the voice.

8. The ultrasound diagnostic apparatus according to claim 4,
  wherein the mode switching operation for switching from the full-screen display mode to the normal screen display mode is a touch operation on a screen of the monitor or an input operation of a predetermined second voice different from the first voice.

9. The ultrasound diagnostic apparatus according to claim 5,
  wherein the mode switching operation for switching from the full-screen display mode to the normal screen display mode is a touch operation on a screen of the monitor or an input operation of a predetermined second voice different from the voice.

10. The ultrasound diagnostic apparatus according to claim 2,
  wherein the processor is further configured to detect a shake operation on the diagnostic apparatus main body or the ultrasound probe,
  the mode switching operation for switching from the full-screen display mode to the normal screen display mode is the shake operation.

11. The ultrasound diagnostic apparatus according to claim 10, further comprising:
  a vibration sensor configured to detect a vibration of the diagnostic apparatus main body or the ultrasound probe, wherein the processor is further configured to detect the shake operation based on the vibration of the diagnostic apparatus main body or the ultrasound probe that is detected by the vibration sensor.

12. The ultrasound diagnostic apparatus according to claim 10,
wherein the processor is further configured to detect the shake operation by analyzing ultrasound images including a plurality of continuous frames.

13. The ultrasound diagnostic apparatus according to claim 3,
wherein the mode switching operation for switching from the full-screen display mode to the normal screen display mode is the shake operation.

14. The ultrasound diagnostic apparatus according to claim 1,
wherein the processor is further configured to
recognize a type of the ultrasound probe,
in the full-screen display mode, perform a display according to the type of the ultrasound probe on the monitor.

15. The ultrasound diagnostic apparatus according to claim 1,
wherein the processor is further configured to
control transmission of an ultrasound beam and reception of an ultrasound echo by the ultrasound probe,
in the full-screen display mode, change a position of a transmission focus of the ultrasound beam according to a display depth of the ultrasound image on the monitor.

16. A control method for a handheld type ultrasound diagnostic apparatus including an ultrasound probe and a diagnostic apparatus main body connected to the ultrasound probe, the method comprising:
generating an ultrasound image based on a reception signal acquired by using the ultrasound probe;
performing switching between a normal screen display mode and a full-screen display mode by performing a mode switching operation on the diagnostic apparatus main body or the ultrasound probe, the normal screen display mode being a mode in which the generated ultrasound image and an operation panel for operating the ultrasound diagnostic apparatus are displayed on a monitor of the diagnostic apparatus main body and an operation of the ultrasound diagnostic apparatus is performed via the operation panel, and the full-screen display mode being a mode in which only the generated ultrasound image is displayed on the monitor and an operation of the ultrasound diagnostic apparatus by using a voice is possible; and
performing different operations for a specific touch operation on the ultrasound image from a user between the normal screen display mode and the full-screen display mode.

17. A processor for a handheld type ultrasound diagnostic apparatus that includes an ultrasound probe and a diagnostic apparatus main body connected to the ultrasound probe, the processor being configured to execute a process comprising:
generating an ultrasound image based on a reception signal acquired by using the ultrasound probe;
performing switching between a normal screen display mode and a full-screen display mode by performing a mode switching operation on the diagnostic apparatus main body or the ultrasound probe, the normal screen display mode being a mode in which the generated ultrasound image and an operation panel for operating the ultrasound diagnostic apparatus are displayed on a monitor of the diagnostic apparatus main body and an operation of the ultrasound diagnostic apparatus is performed via the operation panel, and the full-screen display mode being a mode in which only the generated ultrasound image is displayed on the monitor and an operation of the ultrasound diagnostic apparatus by using a voice is possible; and
performing different operations for a specific touch operation on the ultrasound image from a user between the normal screen display mode and the full-screen display mode.

* * * * *